United States Patent [19]

Giampapa

[11] Patent Number: 5,326,568
[45] Date of Patent: Jul. 5, 1994

[54] METHOD OF TISSUE-SPECIFIC DELIVERY

[76] Inventor: Vincent C. Giampapa, 87 Valley Rd., Montclair, N.J. 07042

[21] Appl. No.: 876,783

[22] Filed: Apr. 30, 1992

Related U.S. Application Data

[63] Continuation-in-part of Ser. No. 695,107, May 3, 1991, Pat. No. 5,201,728.

[51] Int. Cl.$^5$ .......................... A61F 2/02; A61K 9/22
[52] U.S. Cl. ..................... 424/426; 424/423; 424/424; 604/890.1; 604/892.1; 623/11
[58] Field of Search ............... 424/422, 423, 424, 426; 604/890.1, 892.1; 623/11

[56] References Cited

U.S. PATENT DOCUMENTS 3,625,214 12/1971 Higuchi ............................. 424/424

FOREIGN PATENT DOCUMENTS 2424169 12/1974 Fed. Rep. of Germany .

Primary Examiner—Thurman K. Page
Assistant Examiner—C. Azpuru
Attorney, Agent, or Firm—M. K. Silverman

[57] ABSTRACT

The method of tissue-specific delivery of therapeutic agents via a bio-oncotic pump which includes the steps of furnishing an implantable element which is biodegradable in situ within human tissue. Such an element defines a series of respective concentric shells having different therapeutic agents disposed upon each of the shells such that the outermost shell and associated agents will be delivered earliest, while the innermost shell and its agents will be delivered last. The material of the biodegradable element is selected from the group of materials including processed sheep dermal collagen, Hench's bioglass, fibrinogen, polyimino-carbonate, and polylactic acid. A vaso-inductive agent is integrated into the surface of the element. Selected groups of therapeutic agents are incorporated into the element, which is followed by the subcutaneous implantation and securing of said element into the human tissue at the site of interest. Following implantation of the element, the vaso-inductive agent will stimulate capillary growth to facilitate delivery of the therapeutic agent to the tissue specific site.

7 Claims, 5 Drawing Sheets

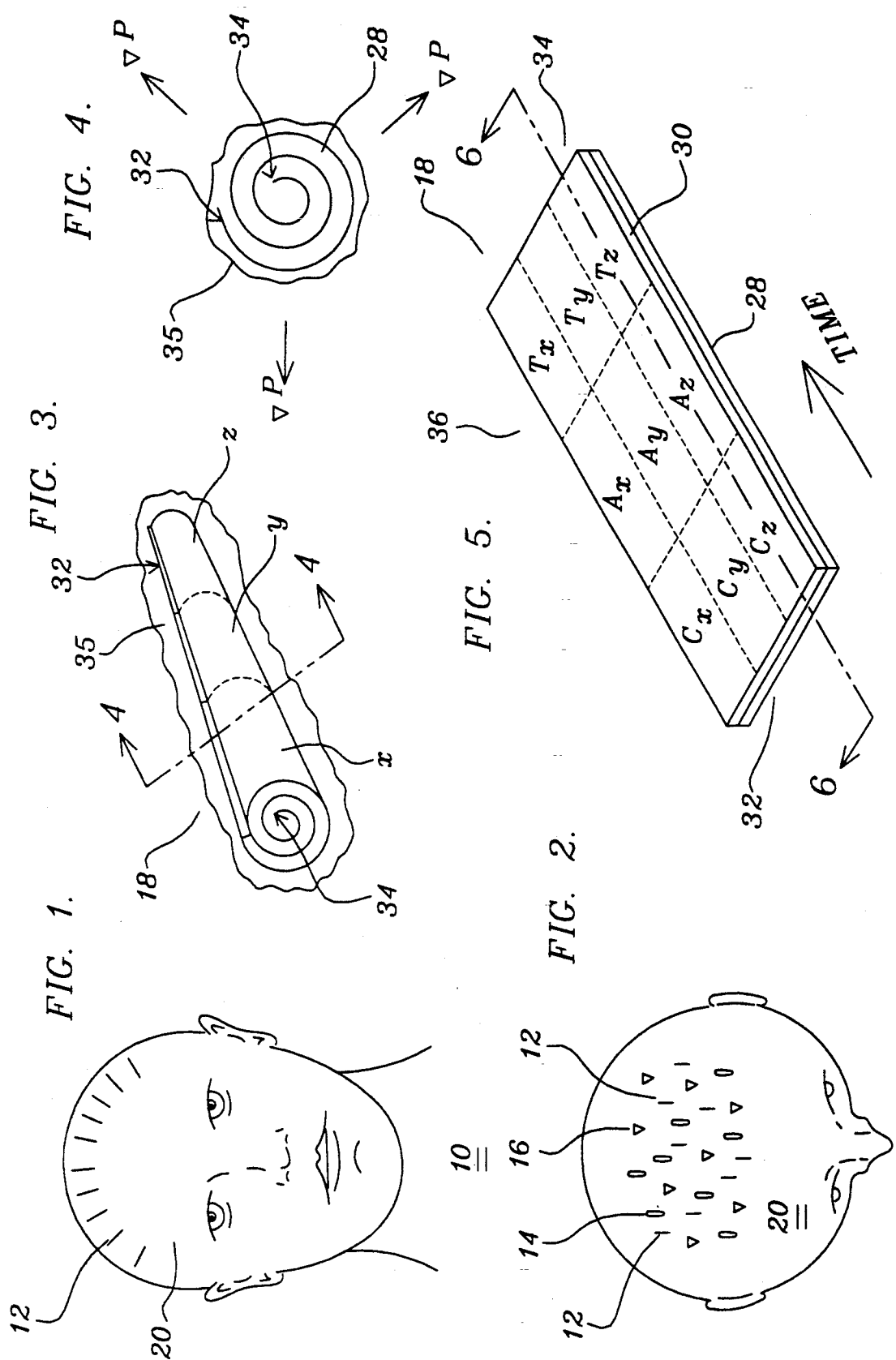

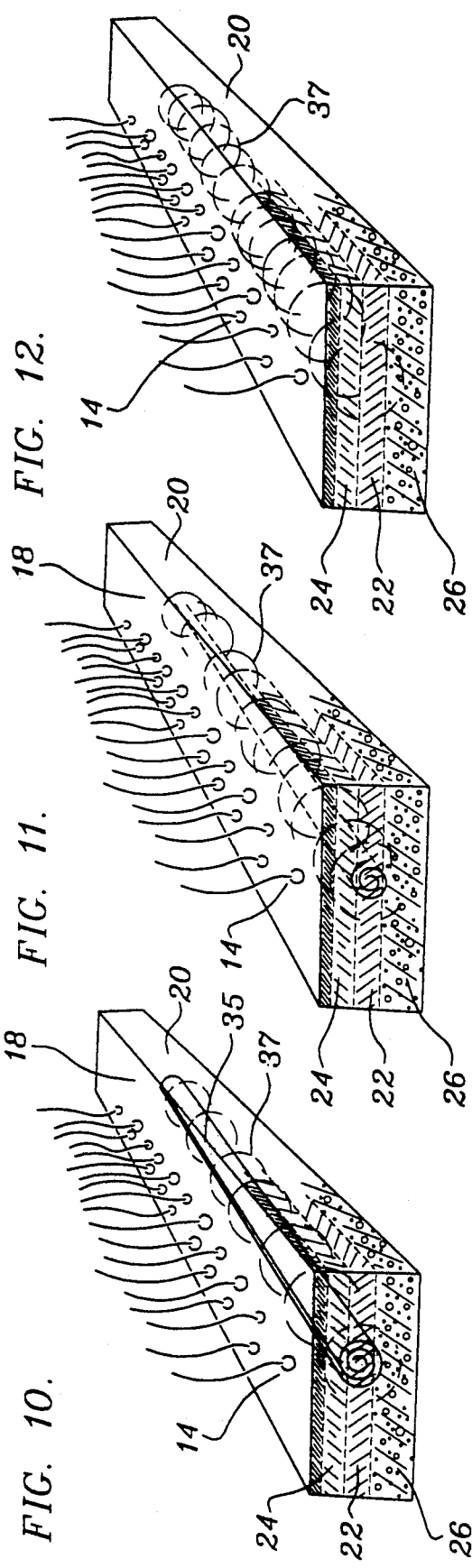
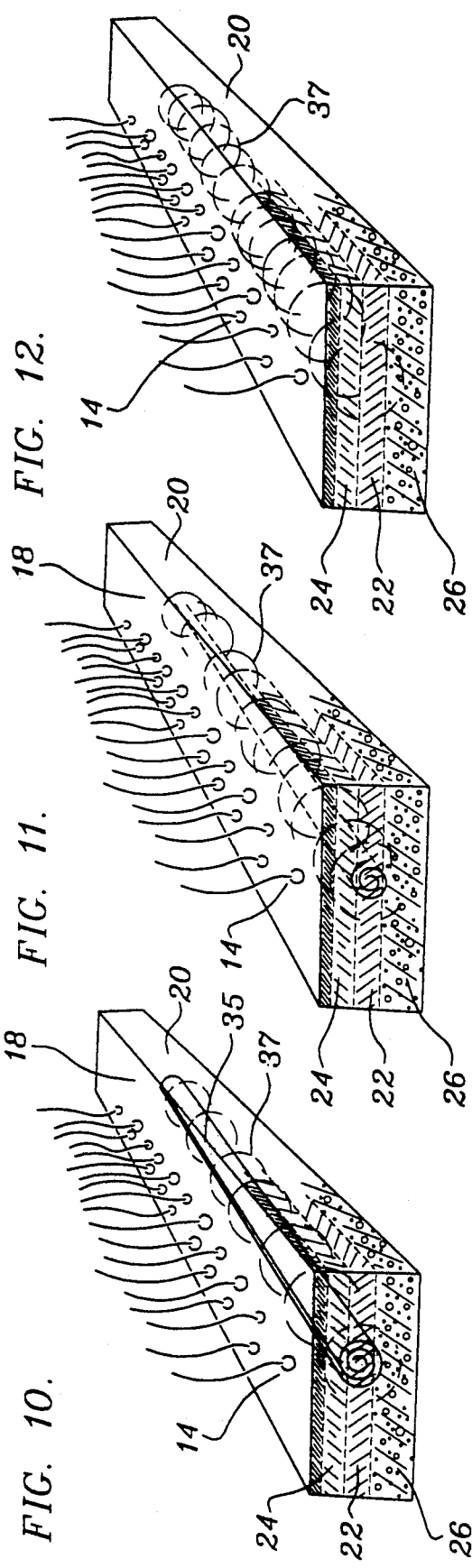
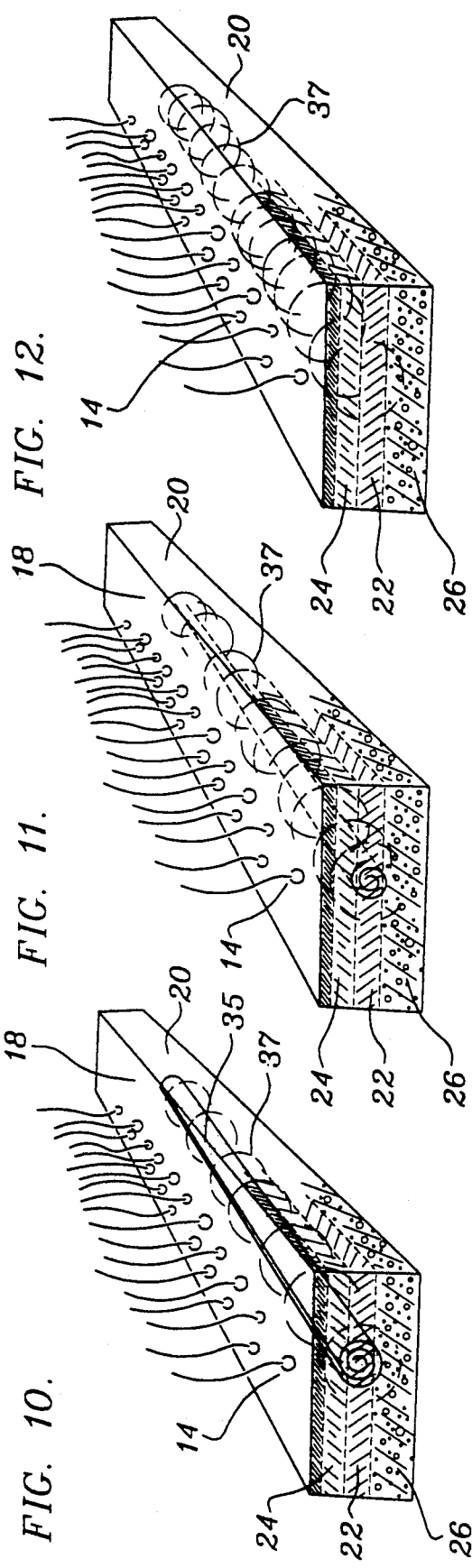
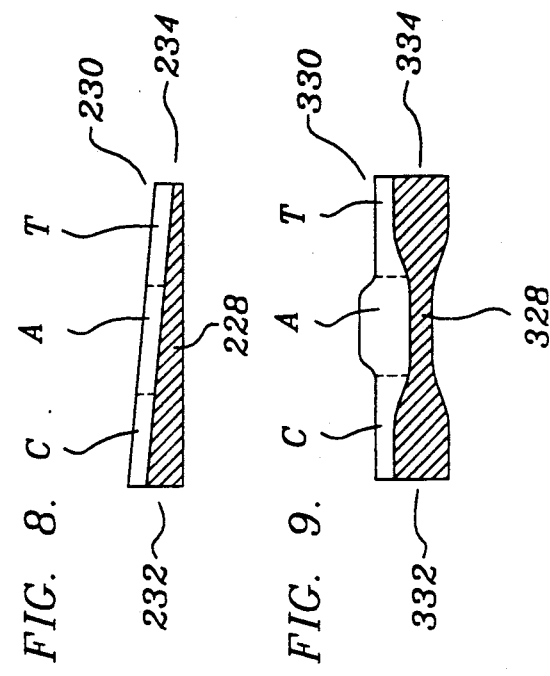
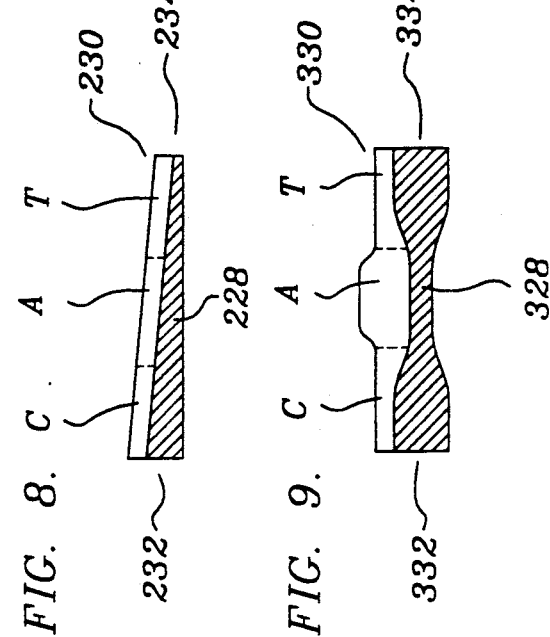
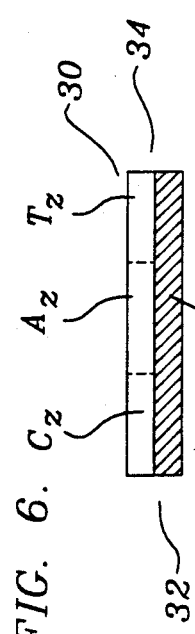
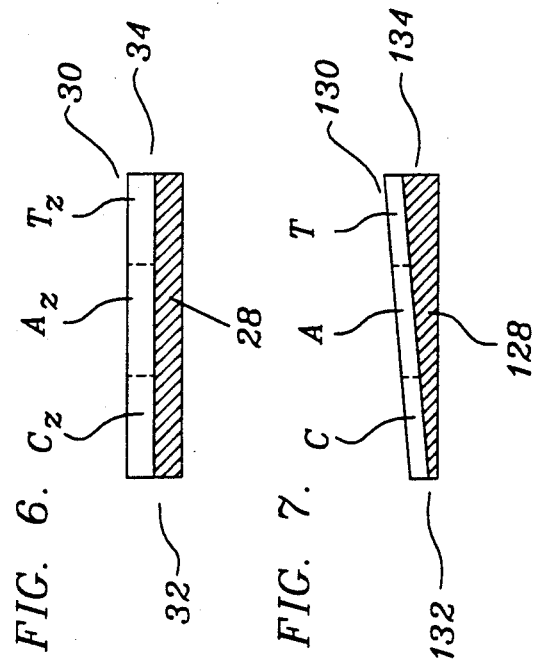

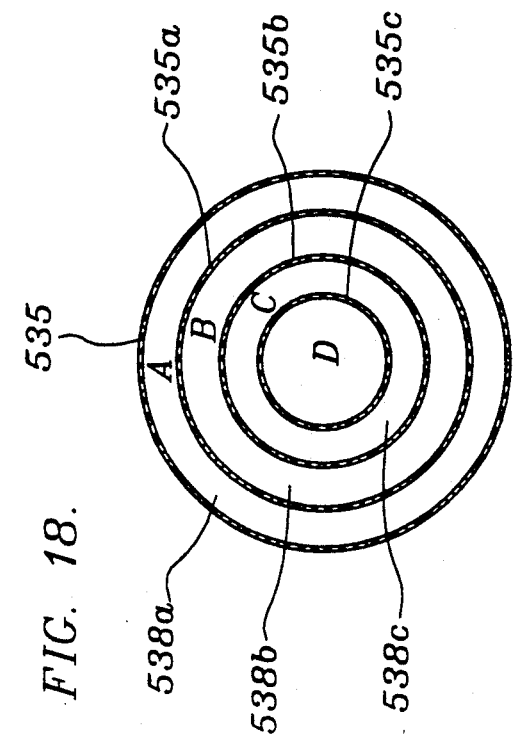
FIG. 17.
FIG. 18.
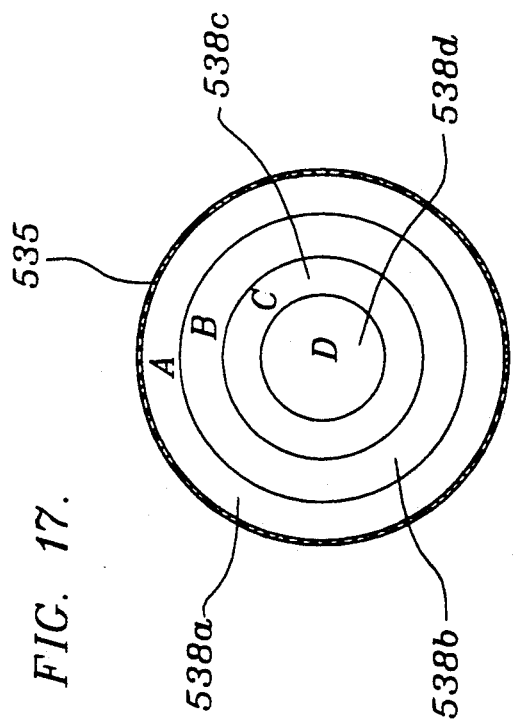
FIG. 19.
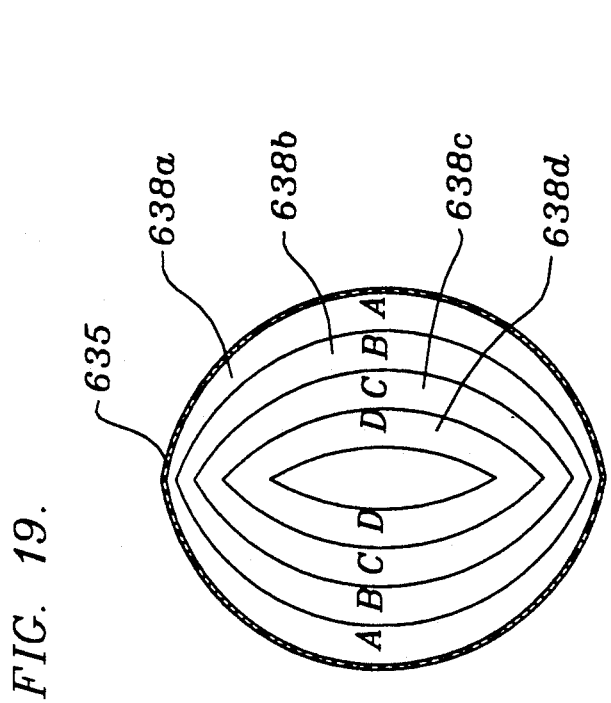
FIG. 20.

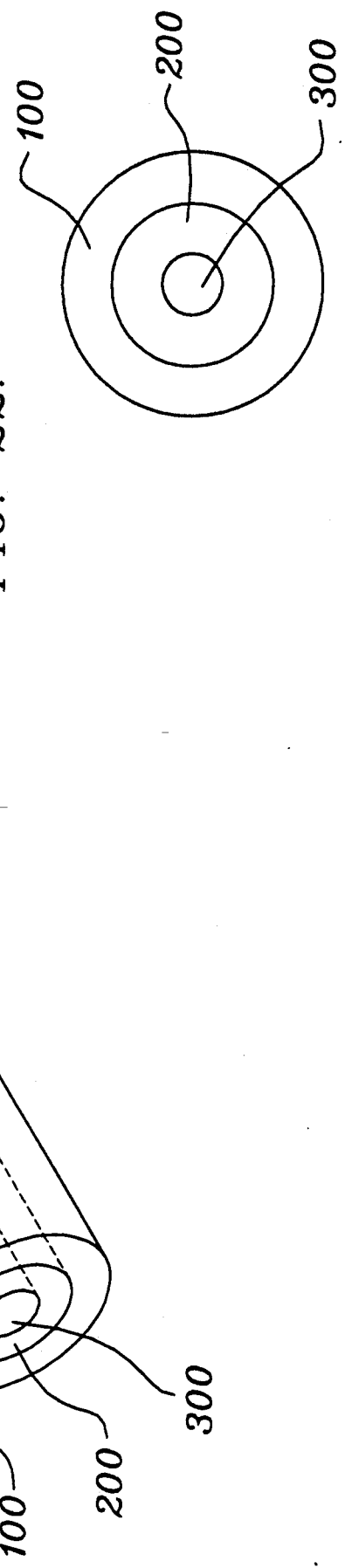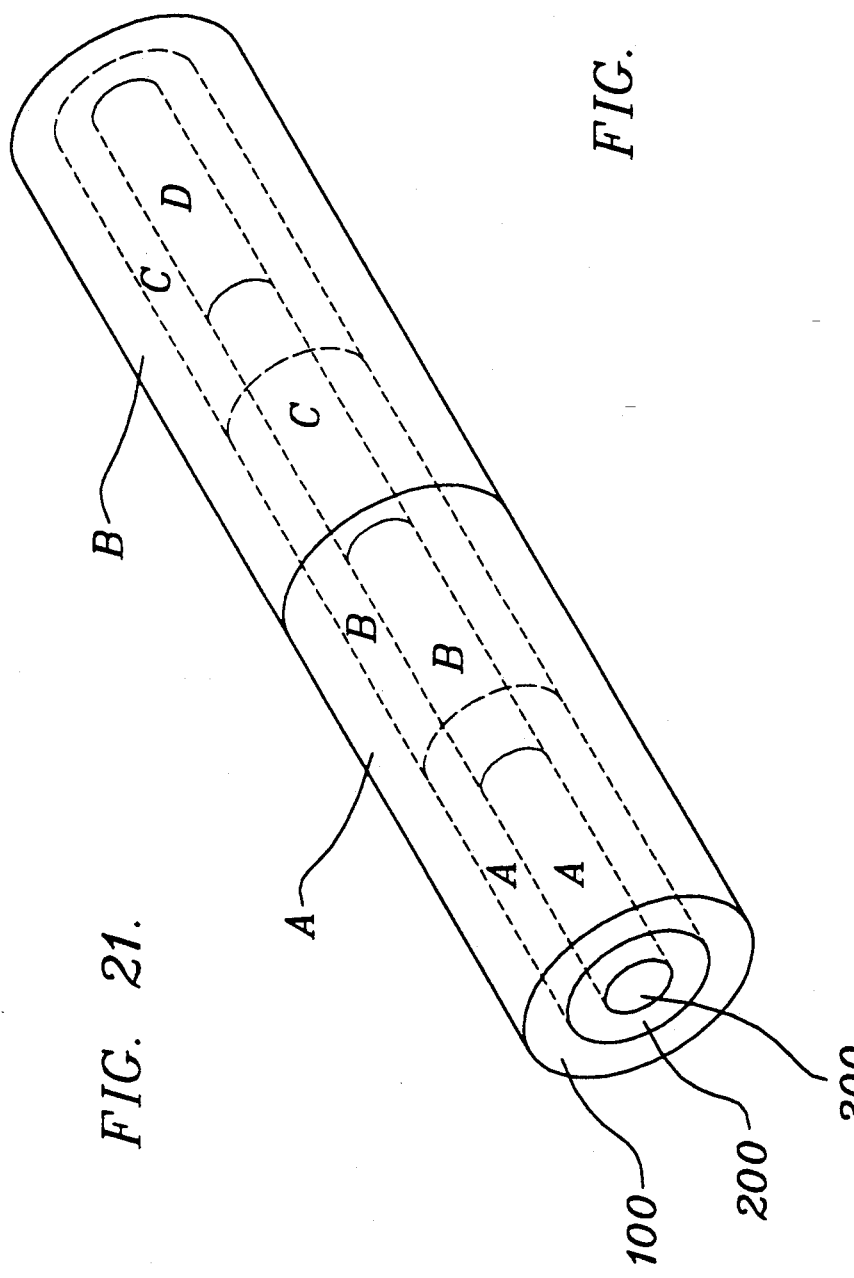

METHOD OF TISSUE-SPECIFIC DELIVERY

REFERENCE TO RELATED APPLICATION

This case is a continuation-in-part of application Ser. No. 07/695,107, filed May 3, 1991, now U.S. Pat. No. 5,201,728.

BACKGROUND OF THE INVENTION

Biodegradable materials have been known in the art for a number of years. More particularly, in the literature of medical research relative to such materials reference is made to the following biodegradable materials:

Processed sheep dermal collagen (PSDC), Hench's bioglass, surgical grade polyurethanes, fibrinogens, polyimino-carbonates, and poly (L-lactic) acid (also known as polylactic acid).

Representative articles in the literature relative to the above are: "Structure and Property Relationships for Design of Polyiminocarbonates", by Pulapura, et al, *Biomaterials*, 1990 (119): 666-78, "Rate Controlled Drug Delivery Systems: Controlled Release versus Sustained Released" by Chien in *Medical Progress Technology* 1989, 15 (1-2): 11-14; and "Enzymatic Activity Toward Poly L-Lactic) Acid Implants by Schakenraad, et al, *Jour. Biomedical Materials Research*, 1990 May, 24(5): 529-45

Much publicity has attended the so-called Norplant elements employed as birth control means and, as such, the Norplant has become well known among contemporary biodegradable materials.

Accordingly, medical research has now established, beyond question, the value of subcutaneous, and other implantation of therapeutic and pharmacologic agents within a biodegradable carrier to facilitate the potentiation or concentration of the agent within cellular tissue at a location which will maximize its benefit to the patient. The present invention is accordingly concerned with an improvement in the form and structure of a biodegradable drug carrier and, particularly, a biodegradable drug carrier which will have application in providing appropriate nourishment to the human scalp or body skin by means of enhanced delivery of necessary nutrients and pharmakinetics.

SUMMARY OF THE INVENTION

The present invention provides for a biodegradable substrate upon which is applied a bioactive or pharmakinetic agent. Where a plurality of different agents are employed, the various agents are applied in a matrix-like fashion upon the substrate. The substrate is then rolled about a major or time axis thereof such that, in a cross-section taken radially from said axis, there is defined a spiral cross-section. Upon the surface of the rolled substrate is applied a vascular growth factor or other vasoinductive growth agent. The biodegradable device, after subcutaneous implantation, will degrade from its outside to inside. As such radial degradation occurs the bioactive material upon the biodegradable substrate will enter capillary and vascular blood flow which is enhanced by the vascular growth factor. The pharmakinetic agent located at the outer portions of the spiral structure will be first to enter adjoining capillaries while those agents upon the portion of substrate nearer to the center of the spiral will be the last to reach adjoining tissue. A timed release of the pharmakinetic agent is thereby obtained as a function on the radial position of the substrate at which the agent is adhered.

It is thereby an object of the present invention to provide an implantable biodegradable pharmakinetic agent release system.

It is another object to provide an in vivo drug release system in which releases thereof may be achieved over an extended period of time and in which particular drug mixes may be varied as a function of time.

It is a further object of the invention to provide a biodegradable implant for delivery of different bioactive agents over respectively differing time intervals, at a specific physiological site.

It is yet another object to provide a subcutaneously implantable biodegradable implant suitable for use in the human scalp or skin to provide nourishment and/or medication to the scalp and its associated system of hair follicles.

The above and yet other objects and advantages of the present invention will become apparent from the hereinafter set forth Brief Description of the Drawings, Detailed Description of the Invention and Claims appended herewith.

BRIEF DESCRIPTION OF THE DRAWINGS

FIG. 1 is a front perspective view showing a patient in whose scalp incisions have been made prior to implantation of the inventive delivery system.

FIG. 2 is a top view of FIG. 1 showing additionally the location of hair implantation structures between the incisions shown in FIG. 1.

FIG. 3 is a perspective view of the implantable biodegradable agent delivery system, showing its vasoinductive exterior and spiral structure.

FIG. 4 is a cross-sectional view taken along the Line 4—4 of FIG. 3.

FIG. 5 is a perspective view showing the "unrolled" substrate of the system and its matrix of bioactive agents.

FIG. 6 is a cross-sectional view taken along Line 6—6 of FIG. 5.

FIG. 7 is a view similar to FIG. 6 showing a second type of substrate.

FIG. 8 is a view similar to FIG. 6 showing a third type of substrate.

FIG. 9 is a view similar to FIG. 6 showing a fourth type of substrate and different mode of layering of the bioactive agents.

FIG. 10 is a first sequential view showing the system following implantation into the scalp.

FIG. 11 is a second sequential view of the view of FIG. 10 showing the implant partially dissolved, with formation of a vascular bed.

FIG. 12 is a third sequential view of the view of FIG. 10 showing the implant fully dissolved, with complete formation of a vascular bed.

FIGS. 17 and 18 are views of a spherical embodiment.

FIGS. 19 and 20 are views of an embodiment having the general structure of an artichoke.

FIG. 21 is a view of a further embodiment of the invention comprising a plurality of concentric tubules.

FIG. 22 is an axial end view of FIG. 21.

DETAILED DESCRIPTION OF THE INVENTION

Figure 13:
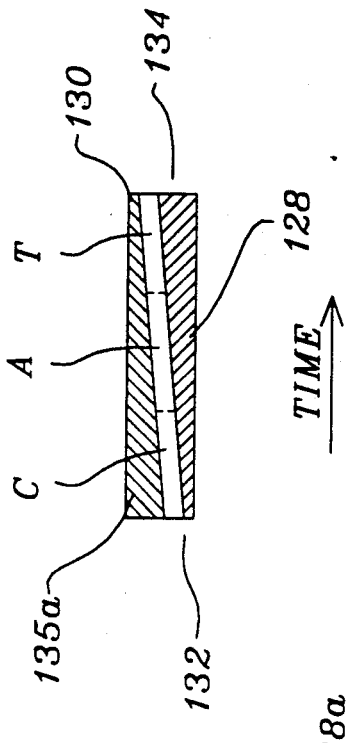
FIGS. 13 and 14 are views similarly to FIG. 7 but showing other embodiments thereof.

With reference to FIG. 1 there is shown, in front perspective view, a patient 10 having scalp 20 in which have been placed incisions 12, preparatory to a hair implant procedure.

FIG. 2 is a top view of the patient 10 of FIG. 1 showing, between incisions 12, various types of hair implantation structures 14 and 16. Such structures 14 and 16 may comprise hair follicles taken from other areas of the patient's own scalp (known as homographs), may comprise a synthetically created hair implant such as the type set forth in my co-pending application Ser. No. 07/796,376, or may comprise a combination of homographs and synthetically created hair implants.

The insertion of the inventive biodegradable timed release implants 18 between such hair structures or normally occurring or thinning hair follicles, acts to provide required nutrition, including amino acids, hormones or drugs such as minoxidyl, in the form of polypeptides, to the newly implanted hair structures or to the normal scalp. See FIGS. 3 to 6. It is to be appreciated that implants 18 may be employed to provide necessary nutrition and other bioactive agents to otherwise healthy hair to increase the thickness thereof as well as to reduce possible hair loss.

With reference to FIGS. 3 to 5, it may be seen that each implant 18 exhibits, in radial cross-section, a spiral structure. This structure is achieved through the use of an initially flat substrate 28 of biodegradable material selected from the group of materials set forth in the Background of the Invention above. Upon the biodegradable substrate 28 is affixed a layer of bioactive material 30 such as a nutrient, a polypeptide, an amino acid, a drug, or other pharmakinetic agent. As relates to the stimulation of hair growth, the bioactive material of choice would be particular polypeptides. Different polypeptides correspond to different stages of the hair growth cycle, in which the initial stage of hair growth is affected by a first polypeptide during the categen phase. An intermediate or second polypeptide operates during the anegen phase, and a third polypeptide operates during the telegen phase.

The first polypeptide or bioactive substance is placed near the outer edge 32 of the substrate 28 as is shown in FIGS. 4 to 6, wherein the various categen-related polypeptides are indicated by the letters Cx, Cy and Cz. It is noted that edge 32 represents the outermost portion of the spiral structure of implant 18 while edge 34 represents the innermost portion of the spiral.

With further reference to FIG. 5, the anegen-related polypeptides, indicated by the letters Ax, Ay and Az, are disposed towards the center of the spiral structure, while the telegen-related polypeptides, denoted by letters Tx, Ty and Tz, are positioned near the core or inner edge 34 of the implant. Accordingly, when the biodegradable substrate 28 is rolled into the structure shown in FIGS. 3 and 4, the categen-related polypeptides will be outermost in location, the anegen-related intermediate in location, and the telegen-related furthest from the exterior of the structure. Thereby, as substrate 28 degrades, for example within the subcutaneous border of the scalp, first polypeptides will be released for an initial period of time, e.g., 10 days. Thereafter, second polypeptides will be released for a period of about 10 additional days and, finally, third polypeptides will be released for a period of about 20 additional days until the entire structure has dissolved. It is noted that the quantity and sequence of polypeptides can be altered depending upon desired effect upon each phase of the hair growth cycle.

For example, it may be desirable to release the pharmakinetic agent during the categen phase to induce a shortening of the categen phase of the hair growth cycle. Conversely it may, in another use, be advantageous to deliver an agent to lengthen the anegen phase of hair growth. In another case, one may wish to induce the hair follicles to move from telegen to anegen phase sooner than would be genetically instructed. All of the above can be achieved by adjustments in the selection of phase-related polypeptides as agents Cx, Cy, Cx, Ax, Ay, Ax, Tx, Ty and Tz on substrate 28.

With further reference to FIGS. 3 and 4, the external surface of implant 18 is provided with a coating 35 of a vasoinductive or angiogenic agent, such as a vascular growth factor. Suitable growth factors of this type include vascular endothelial growth factor, platelet growth factor, vascular permeability factor, fibroblast growth factor, and transforming growth factor beta. Also certain polypeptides have been demonstrated to be vasoinductive and/or angiogenic.

Through the use of such a system, the vascular system of the scalp, which comprises a network of capillaries and supportive tissue within the scalp, will be nourished and increased in density thereby strengthening existing hair follicles and providing necessary polypeptides and other bioactive agents to the existing hair follicles. Such increased capillary density will increase the oncotic and osmotic pressure outwardly from the implant thereby facilitating transfer of the pharmakinetic agent to the adjoining tissue. This is indicated by the symbols P in FIG. 4.

In FIG. 10 is shown implant 18, already placed within an incision 12 in which the incision has been closed into scalp 20. Also shown are hair structures 14. Therein it may be seen in that a capillary bed 37 has started to form as a result of the action of the vasoinductive coating 35.

It is further noted that the location of implant 18 is at the bottom of dermis 22, below eperdimis 24 and above muscle tissue 26. The location comprising the interface between dermis 22 and muscle tissue 26 is often referred to as the subcutaneous border, this location being that at which the greatest flow of microcapillary blood occurs and that at which the greatest concentration of follicles normally exists. The dots shown within implant 28 represent bioactive material 30.

In the sequential view of FIG. 11 implant 18 is shown in a partially dissolved stage, and in the view of FIG. 12 is shown in a fully dissolved stage. At the stage of FIG. 11 the capillary bed 37 is more evident as the implant 18 has partially dissolved while delivering the agent of the substrate matrix. By FIG. 12 the implant is fully dissolved but the capillary bed remains, providing enhanced blood flow at the implantation sites 12. Drug delivery has been completed at this point.

It is to be understood that the above described implantable biodegradable bioactive agent delivery system is not limited to the needs of the scalp but, rather, may find application in numerous other medical and biological environments in which the timed release of a plurality of bioactive agents, each within particularly designated time intervals is necessary, i.e., the delivery of local cancer inhibiting medications, combinations of chemotherapeutic drug regimens, or analgesies on a long term basis. Other pharmakinetic agents usable with the present system include hormones, enzymes, catalysts, anesthetics, antibiotics, anti-inflammatories, immunoglobulins and free-radical scavengers.

With reference to FIGS. 6 to 9 it is to be appreciated that the thickness of edge 36 of substrate 28 of implant 18 may also be varied. For example, as is shown in the side cross-sectional view of FIG. 7, if one wishes to increase the duration of delivery of a bioactive agent 130 relative to the duration during which an agent 131 is delivered, end 132 of substrate 128 may be thickened while end 134 may be made narrower, this meaning that agent 130 would be released more slowly into the delivery site, while agent 131 would be delivered more quickly.

Should one wish to achieve the reverse effect, a structure of the type shown in FIG. 8 would be used in which edge 232 of biodegradable substrate 228 would be narrowed while edge 234 of the substrate would be thickened, thereby providing for faster delivery of agent 230 at the beginning of the biodegrading of the implant and a slower delivery of agent 231 toward the end of the action of the implant.

It is noted that the rate of dissolution of respective areas of substrate 28 may also be regulated by varying the internal binding characteristic of the biodegradable substrate in such respective areas of the matrix thereof.

With reference to FIG. 9 there is shown a system in which a pulse of material A in layer 330 may be provided by increasing the thickness thereof at the desired time interval of the pulse, while decreasing the thickness of substrate 328 during this time interval.

With regard to the embodiment of FIG. 13, it may be seen that, using the structure of FIG. 7 as a basis, a layer of vasoinductive agent 135 may be applied to the bottom of biodegradable substance 128. In this arrangement, in addition to the effect of the above described outer coating of vasoinductive agent, is be provided, internal to the spiral structure the vasoinductive agent 125 within the spiral of the cross-section of the structure. This provision of vasoinductive agent 135 along the time axis of the structure will assure that a greater amount of the vasoinductive agent is released during the early stages of operation of the delivery means, thereby assuring an initially rapid build-up of the capillary bed.

Figure 14:
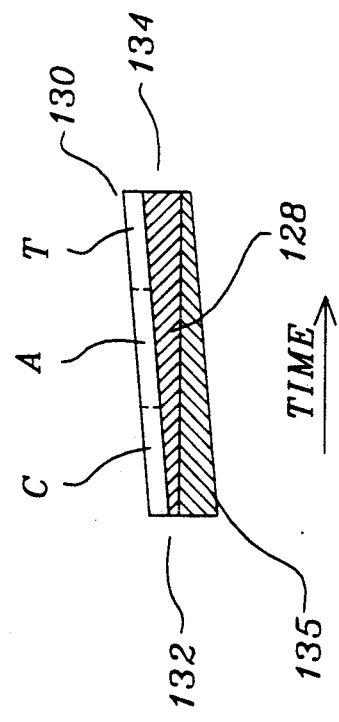

A variant of the embodiment of FIG. 13 is shown FIG. 14. Therein a layer of vasoinductive agent 135a is applied above the layer 130 of the pharmakinetic agents C, A, and T manner of operation of this embodiment being in all other respects the same as that of the embodiment of FIG. 13.

Figure 15:
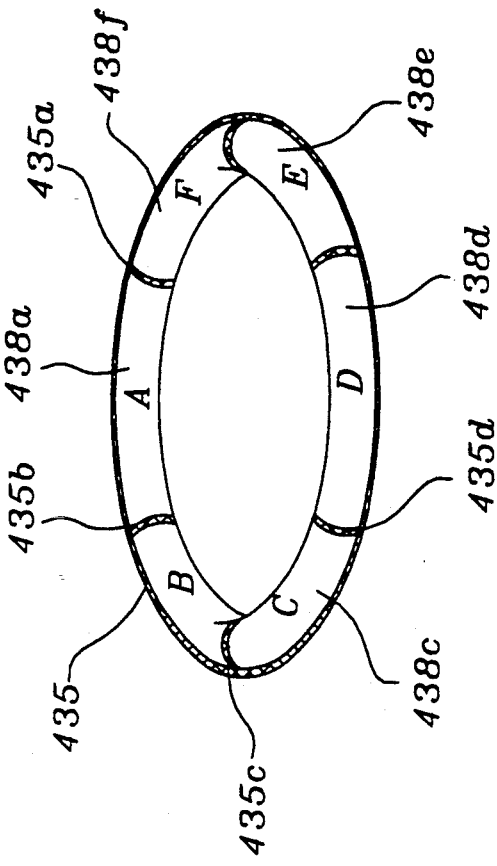
FIGS. 15, 15a, and 16 are views of a toroidal embodiment of the invention.
Figure 15A:
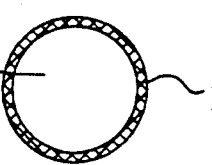

With respect to FIG. 15 it is noted that a biodegradable substrate 438 may assume the form of a ring or toroid having a number of polar segments 438a thru 438f, in which each of said segments may contain a different pharmakinetic agent imbedded in segments 438 while each segment is surrounded by vasoinductive agent 435. This embodiment is useful where a plurality of different pharmakinetic agents are needed for delivery at the same time. It is to be appreciated that within the scope of this embodiment, each of the polar segments may extend to the center so that the entire structure would proximate that of a disk.

Figure 16:
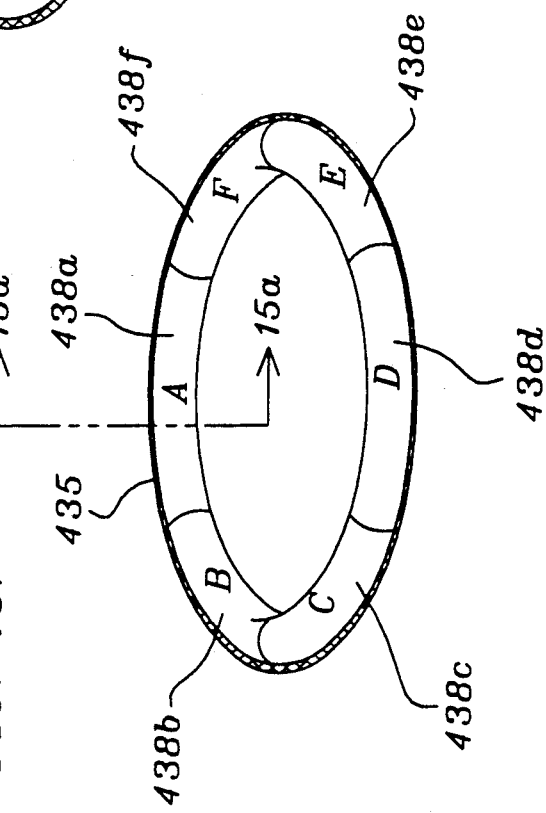

In the embodiment of FIG. 16, radial segments 435a through 435f may be added to the structure of FIG. 15 to provide for more extensive capillary growth. Therefore, in the event that the radii of the substrate segments 438 a thru f were extended toward the center the length of vasoinductive agents 435a thru 435f would likewise be extended.

With reference to the embodiment of FIG. 17 there is shown a cross-section of a spherical structure consisting of a plurality of radial concentric substrate 538a thru 538d (layers A to D) surrounded, upon the outer surface thereof, by vasoinductive layer 535. This embodiment may generally be understood as a spherical embodiment of the above-described embodiment of FIGS. 3 thru 6, wherein the first to be delivered pharmakinetic agent is applied to layer A, the second to layer B and the third to layer C and the last agent to be delivered to core D.

The embodiment of FIG. 18 is similar to that of FIG. 7; however, there is applied, to the surface of each biodegradable layer 538a thru 538d, a respective layers of vasoinductive agents, 535a thru 535c respectively such that, at each point of radial dissolution of the respective layers 538 of the implant a new region of vasoinductance, i.e., capillary structure will be formed.

With reference to the embodiment to of FIG. 19 there is shown an artichoke-like structure consisting of a plurality of symmetric leaf-like substrates 638a thru 638d which are surrounded by an external vasoinductive layer 635. The embodiment of FIG. 19 operates in principle similar to that of the embodiment of FIG. 17, however, will be useful where a longer or flatter geometry is more suitable to the particular anatomical site. It is, accordingly, to be understood that the geometry of FIG. 19 may be considerably elongated or flattened versus that shown.

In the embodiment of FIG. 20, internal vasoinductive layers 635a thru 635c are applied to said leaf-like substrates 638a thru 638d described in reference to FIG. 19. In other respects, the operation of the embodiment of FIG. 20 follows that above described with reference to the embodiment of FIGS. 18.

In the embodiment of FIGS. 21 and 22 there is shown a method of construction of a tubule of the type above discussed with reference to FIGS. 3 thru 5, however, in which the construction thereof is accomplished by means of a plurality of concentric, hollow tubules 100, 200 and 300. Comparing the embodiment of FIGS. 21 and 22 with the embodiment of FIGS. 3 to 5, it is to be appreciated that the outermost tubular 100 corresponds in function to the outermost edge 32 of substrate 28, the function of the middle tubule 200 corresponds to that of central area Ax, Ay and Az of substrate 28, while the function of innermost tubule 300 corresponds to that of the area of innermost edge 34 of substrate 28 which is the innermost portion of the spiral structure of the embodiment of FIGS. 3 to 5.

In the context of said embodiments, the categen-related polypeptides Cx, Cy and Cz would be placed upon outer tubule 100, the anegen-related polypeptides Ax, Ay and Az upon the intermediate tubule 200, and the telegen-related polypeptides Tx, Ty and Tz positioned upon the innermost tubule 300.

As may be noted by the Letters A and B in FIG. 1, each of said tubules may be divided into two or more segments to provide for varying types of polypeptides. The embodiment of FIGS. 21 to 22 will, accordingly, operate, as a practical matter, in the same fashion as the spiral "jelly roll" embodiment of FIGS. 3 to 5.

The embodiment of FIGS. 21 and 22 is also closely related in structure to the embodiments of FIGS. 17 and 18.

Accordingly, while there has been shown and described the preferred embodiment of the instant invention it may be appreciated that the invention it may be appreciated that the invention may be embodied otherwise than is herein specifically shown and described and that within said embodiment, certain changes may be made within the forms and arrangements of the parts without departing from the underlying ideas or principles of this invention within the scope of Claims appended herewith.

Having thus described my invention what I claim as new, useful and non-obvious and, accordingly, secure by Letters Patent of the United States is:

1. A method of bio-oncotic tissue-specific delivery of therapeutic agents, comprising the steps of:
   (a) furnishing an implantable element that is biodegradable in situ within human tissue, said implantable element defining a series of respectively concentric shells having said therapeutic agents incorporated upon or within each of said shells such that the outermost shell and said agents associated therewith will be delivered earliest while the innermost shell and its agents will be delivered last within said human tissue, said agents to be delivered selected from the group consisting essentially of chemotherapeutics, analgesics, hormones, enzymes, anesthetics, anti-inflammatories, antibiotics, and immunoglobulins, and the material of said biodegradable element selected from the group consisting essentially of processed sheep dermal collagen, Hench's bioglass, fibrinogen, polyimino-carbonates, and polylactic acid;
   (b) integrating into a surface of said element a vasoinductive agent selected from the group consisting essentially of vascular endothelial growth factor, platelet growth factor, vascular permeability growth factor, fibroblast growth factor, and transforming growth factor beta; and
   (c) subcutaneously implanting and securing said element into said tissue,
   whereby, following implantation of said element into said tissue, said vaso-inductive agent will stimulate capillary growth thereby facilitating delivery of said therapeutic agents to said tissue.

2. The method as recited in claim 1, in which said implantable element furnishing step (a) comprises:
   providing a planar substrate rolled spirally upon an axis thereof to approximate the external geometry of a cylinder.

3. The method as recited in claim 1 in which said implantable element furnishing Step (a) comprises:
   furnishing a series of respectively concentric shells having different therapeutic agents disposed upon each of said shells such that the outermost shell and associated agents will be delivered earliest while the innermost shell and its agents will be delivered last to the human tissue.

4. The method as recited in claim 3, further comprising the step of:
   (e) providing further vasoinductive agents disposed between each of said concentric shells.

5. The method as recited in claim 3, in which said step of furnishing concentric shells comprises the step of:
   furnishing concentric tubules.

6. The method as recited in claim 5, further comprising the step of:
   (f) providing further vasoinductive agents disposed between each of said concentric tubules.

7. The method as recited in claim 1, in which said integrating Step (b) comprises:
   use of an angiogenic agent as said vasoinductive agent.

* * * * *